United States Patent [19]

Wong et al.

[11] Patent Number: 5,597,906
[45] Date of Patent: Jan. 28, 1997

[54] CARBON LINKED GLYCOSYL COMPOUNDS

[75] Inventors: Chi-Huey Wong, Rancho Sante Fe; Hirosato Kondo, San Diego, both of Calif.

[73] Assignee: The Scripps Research Institute, La Jolla, Calif.

[21] Appl. No.: 33,608

[22] Filed: Mar. 18, 1993

[51] Int. Cl.$^6$ ..................................... C07H 15/00
[52] U.S. Cl. .................. 536/1.11; 536/116; 536/117; 536/124
[58] Field of Search ................... 536/117, 5, 8, 536/4.1, 1.1, 1.11, 124, 116

[56] References Cited

U.S. PATENT DOCUMENTS 4,089,606  5/1978  Furuya et al. ........................... 536/5

OTHER PUBLICATIONS

Chemical Abstracts, vol. 67, No. 11, issued 1967, Komatsu et al, "Studies on the constituents of *Swertia japonica*. I. Structures of swertisin and isoswertisin", p. 5073, col. 1, abstract No. 53988t, *Chem. Pharm. Bull.* (Tokyo), 15(3), pp. 263–269 (1967)(Eng).

Chemical Abstracts, vol. 89, No. 19, issued 1978, Ghosal et al, "Differences in the chemical constituents of *Mangifera indica*, infected with *Aspergillus niger* . . . moniliformae", p. 312, col. 1, abstract No. 160297t, *Phytochemistry* 1978, 17(4), 689–94 (Eng).

Chemical Abstracts, vol. 93, No. 19, issued 1980, Eade et al, "C–Glycosylflavonoids. III. The synthesis of 5,7,4'-tri-–O–methyl-vitexin (8–C–β–D–glucopyranosyl–5,7,4'-tri-methoxyflavone)" p. 703, col. 2, abst. No. 186723m, *Aust. J. Chem.* 1979, 32(11), 2483–93.

Chemical Abstracts, vol. 99, No. 11, issued 12 Sep. 1983, Stewart et al, "C–Glycosidation of pyridyl thioglycosides", p. 599, col. 2, abstract No. 88507y, *Tetrahedron Lett.* 1983, 24(27), 2715–18 (Eng).

Chemical Abstracts, vol. 103, No. 3, issued 22 Jul. 1985, Stewart et al, "C–Glycosidation of pyridyl thioglycosides", p. 610, col. 1, abstract No. 22859j, *J. Am. Chem. Soc.* 1985, 107(14), 4289–96 (Eng).

Chemical Abstracts, vol. 109, No. 5, issued 01 Aug. 1988, Schmidt et al, "Glycosyl imidates. 22. C–Glucosylarenes from O–α–D–glucosyl trichloroacetimidates. Structure . . . ", p. 643, col. 1, abstract No. 38080h, *Carbohy. Res.*, 1987, 171, pp. 59–79 (Eng).

*Primary Examiner*—John Kight
*Assistant Examiner*—Everett White
*Attorney, Agent, or Firm*—Donald G. Lewis

[57] ABSTRACT

Carbon linked glycosyl compounds are disclosed and synthesized. The synthesis employs a blocked carbohydrate donor and a blocked glycosyl acceptor. The blocked carbohydrate donor includes an acid labile phosphite leaving group attached to the anomeric carbon. The blocked glycosyl acceptor includes an unprotected carbon susceptible to electrophilic attack. The reaction is initiated by the addition of a Lewis acid so as to activate the acid labile phosphite leaving group on the carbohydrate donor. The substitution reaction may be conducted at −78° C. in a solvent which favors the formation of carbon linked glycosylation products.

7 Claims, No Drawings

CARBON LINKED GLYCOSYL COMPOUNDS

Government Rights

This invention was made with government support under Grant No. GM 44154 awarded by the National Institutes of Health. The U.S. government has certain rights in the invention.

Field of the Invention

The invention relates to compounds having carbon linked glycosyl bonds and to a method for synthesizing such compounds. More particularly, the invention relates to a substitution reaction employing a carbohydrate donor having an acid labile phosphite and an acceptor having an unprotected carbon atom which is susceptible to electrophilic attack.

Background of the Invention

Simple sugars may be categorized as ketoses or aldoses. When ketoses and aldoses undergo ring closure, they form hemiketals and hemiacetals, respectively. In a hemiketal or hemiacetal, the "carbonyl" carbon is attached to a ring carbon and a ring oxygen. The incorporation of the "carbonyl" carbon into the ring structure of the hemiketal or hemiacetal imparts a new chirality, according to the configuration of the substituents. Accordingly, the "carbonyl" carbon of an aldose or a ketose is termed the "anomeric" carbon.

An oxygen linked glycosyl bond is formed when an anomeric carbon of an hemiacetal or hemiketal is condensed with an alcohol to form a ketal or acetal. The condensation reaction creates a glycosyl bond between the anomeric carbon and the alcohol. If both the hemiacetal or hemiketal and the alcohol are monosaccharides, then the resultant acetal or ketal is a disaccharide. The two subunits of the disaccharide are linked through at least one anomeric carbon by a glycosyl bond.

In an acetal, the anomeric carbon is located at a terminal position on the carbon backbone of the aldose. Accordingly, bond linkages with the anomeric carbon of the acetal include a ring carbon, a ring oxygen, a glycosyl oxygen, and a hydrogen.

In a ketal, the anomeric carbon is centered at a non-terminal carbon within the backbone of the ketose. Accordingly, bond linkages with the anomeric carbon of the ketal include a ring carbon, a ring oxygen, a glycosyl oxygen, and a carbon side chain.

Glycosyl bonds may be formed with or without the assistance of enzyme catalysis. Most natural products having glycosyl bonds are formed with the assistance of enzyme catalysis. A broad array of naturally occurring oligosaccharides and polysaccharides are included within this category. Unfortunately, many oxygen linked glycosyl products are subject to enzymic degradation.

Martin et al. (Tetrahedron Letters (1992), 33 (41), pp 6123–6126) disclose a non-enzymic method for forming oxygen linked glycosyl bonds. Martin discloses the use of diethyl phosphite as a leaving group for synthesizing oxygen linked glycosyl bonds.

What is needed is an easily synthesized glycosyl bond which can serve as an analog to oxygen linked glycosylation bonds but which does not employ oxygen as a linkage unit.

Summary

The invention is a substitution reaction employed for producing carbon linked glycosylation products. The substitution reaction employs a blocked carbohydrate donor and a blocked glycosyl acceptor. The blocked carbohydrate donor includes an anomeric carbon with an acid labile phosphite leaving group attached thereto. An example of a preferred carbohydrate donor is dibenzyl 6-deoxy-2,3,4-tri-O-acetyl-β-L-galactopyranosyl phosphite. The acid labile phosphite leaving group is of a type which is activatable by a Lewis acid. An example of a preferred Lewis acid is trimethylsilyl trifluoromethanesulfonate (TMSOTf). A carbohydrate donor is considered to be "blocked" if it is unreactive with its activated form. The blocked glycosyl acceptor includes an unprotected carbon susceptible to electrophilic substitution. An example of a preferred blocked glycosyl acceptor is 1,3,5-trimethoxybenzene. A glycosyl acceptor is considered to be "blocked" if it is unreactive with the activated carbohydrate donor except at the unprotected thio group.

The blocked carbohydrate donor and blocked glycosyl acceptor are admixed in a solvent which promotes the formation of the substitution glycosylation reaction, e.g., $CH_2Cl_2$, as disclosed in the example. The reaction is initiated by the addition of the Lewis acid so as to activate the phosphite leaving group on the donor. The activated donor then reacts with the activated acceptor by means of electrophilic attack to produce a carbon linked glycosyl bond. After completion, the reaction is then quenched. Quenching may be achieved by washing the glycosylation products with saturated $NaHCO_3$.

The invention also includes carbon linked glycosylation products produced by the above synthetic method. Examples of preferred carbon linked glycosylation products include 1-C-(2',4',6'-trimethoxyphenyl)-1,6-dideoxy-β-L-galactopyranose and 1-C-(2',4',6'-trimethoxyphenyl)-1,6-dideoxy-2,3,4-tri-O-acetyl-β-L-galactopyranose.

Detailed Description

A scheme illustrating a carbon linked glycosylation reaction is provided below:

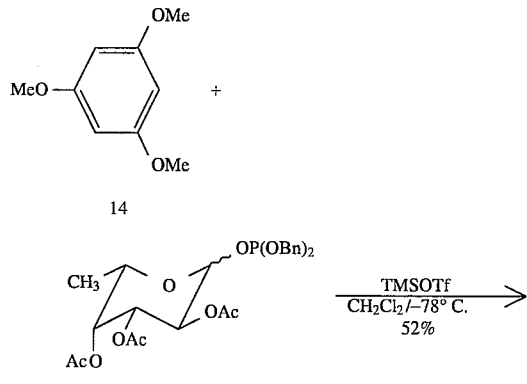

-continued

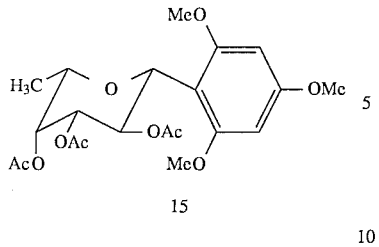

15

EXAMPLE

The blocked glycosyl acceptor, trimethoxybenzene 14, was purchased from Sigma Chemical Company (St. Louis, Mo.). The blocked carbohydrate donor, dibenzyl 2,3,4-tri-O-acetyl-L-fucosyl phosphite 5 was made according to the method of Ichikawa et al. (J. Org. Chem. 1992, 57, 2943). The glycosyl acceptor 14 (14 mg, 0.084 mmol) and the carbohydrate donor 5 (45 mg, 0.084 mmol) were admixed in 1 mL $CH_2Cl_2$ with molecular sieves of approximately 3Å and cooled to −78° C. The acid labile dibenzyl phosphite leaving group on the carbohydrate donor 5 was then activated by the addition of a Lewis acid, e.g. 9 mg, 0.040 mmol of trimethylsilyl trifluoromethanesulfonate (TMSOTf). After stirring the admixture for one hour at −78° C., the reaction was quenched with $Et_3N$ and washed with saturated $NaHCO_3$. The organic solvents were dried over $Na_2SO_4$, filtered, and concentrated under reduced pressure.

The resultant residue was separated by preparative thin layer chromatography (Merck Art 5744, AcOEt/Hexane, 2:3) to give the carbon linked glycosylation product 15, i.e. 1-C-(2',4',6'-trimethoxyphenyl)-1,6-dideoxy-2,3,4-tri-O-acetyl-β-L-galactopyranose. The yield was 52% (20 mg). The product 15 appeared as a colorless oil. If desired, the glycosylation product 13 may be de-acetylated to produce 1-C-(2',4',6'-trimethoxyphenyl)-1,6-dideoxy-β-L-galactopyranose.

The product 15 was subjected to NMR analysis, viz.: $^1$H-NMR (CDCL$_3$) δ; 1.20 (1H, d, J 6.4 Hz, Fuc-CH$_3$), 1.73, 1.99, 2.22 (3H, each s, OAc), 3.781, 3.783, 3.87 (3H, each s, OCH$_3$), 3.87 (1H, q, J 6.4 HZ, H-5), 4.95 (1H, d, J 9.96 Hz, H-1), 5.12 (1H, dd, J 3.4, 9.96 Hz H-3), 5.31 (1H, dd, J 0.8, 3.4 Hz, H-4), 6.05 (1H, d, J 2.2 Hz, phenyl proton), 6.10 (1H, t, J 9.96 Hz, H-2), 6.106 (1H, d, J 2.2 Hz, phenyl proton).

HRMS: Calculated for $C_{21}H_{28}O_{10}Cs$ (M+Cs$^+$) 573.0737; found value was 573.0740.

What is claimed is:

1. A substitution reaction for producing carbon linked glycosylation products comprising the following steps:

Step A: providing a blocked carbohydrate donor having an anomeric carbon with an acid labile phosphite leaving group attached thereto for generating an intermediate susceptible to nucleophilic attack;

Step B: providing a blocked glycosyl acceptor having an unprotected carbon;

Step C: providing a promotor having Lewis acid activity for catalyzing the phosphite leaving group of said Step A; then Step D: reacting the blocked carbohydrate donor of said Step A with the blocked glycosyl acceptor of said Step B in the presence of the promotor of said Step C within a solvent favoring the formation of carbon linked glycosylation products; and then Step E: quenching the reaction of said Step D.

2. A substitution reaction as described in claim wherein: in said Step B, the blocked glycosyl acceptor is 1,3,5-trimethoxybenzene.

3. A substitution reaction as described in claim 1 wherein:

in said Step C, the promotor is trimethylsilyl trifluoromethanesulfonate (TMSOTf).

4. A substitution reaction as described in claim 1 wherein:

in said Step E, quenching is achieved by the addition of $Et_3N$ and is followed by washing the glycosylation products with saturated $NaHCO_3$.

5. A substitution reaction as described in claim 1 wherein:

in said Step A, the phosphite leaving group is dibenzyl phosphite.

6. A substitution reaction as described in claim 5 wherein:

in said Step A, the blocked carbohydrate donor is dibenzyl 6-deoxy-2,3,4-tri-O-acetyl-β-L-galactopyranosyl phosphite.

7. A substitution reaction for producing carbon linked glycosylation products comprising the following steps:

Step A: providing dibenzyl 6-deoxy-2,3,4-tri-O-acetyl-β-L-galactopyranosyl phosphite as a blocked carbohydrate donor having an anomeric carbon with an acid labile phosphite leaving group attached thereto for generating an intermediate susceptible to nucleophilic attack;

Step B: providing 1,3,5-trimethoxybenzene as a blocked glycosyl acceptor having an unprotected carbon;

Step C: providing trimethylsilyl trifluoromethanesulfonate (TMSOTf) as a promotor having Lewis acid activity for catalyzing the phosphite leaving group of said Step A; then Step D: reacting the blocked carbohydrate donor of said Step A with the blocked glycosyl acceptor of said Step B in the presence of the promotor of said Step C within a solvent favoring the formation of carbon linked glycosylation products, wherein the solvent is $CH_2Cl_2$ having a temperature of approximately −78° C. and includes molecular sieves of approximately 3Å; and then Step E: quenching the reaction of said Step D by the addition of $Et_3N$ and is followed by washing the glycosylation products with saturated $NaHCO_3$.

\* \* \* \* \*